United States Patent
Dubach

(10) Patent No.: US 9,656,035 B2
(45) Date of Patent: May 23, 2017

(54) LARYNGEAL MASK HAVING A SUPRAGLOTTIC TUBE

(71) Applicant: Singularity AG, Maur (CH)

(72) Inventor: Werner F. Dubach, Maur (CH)

(73) Assignee: Singularity AG, Maur (CH)

( * ) Notice: Subject to any disclaimer, the term of this patent is extended or adjusted under 35 U.S.C. 154(b) by 296 days.

(21) Appl. No.: 14/405,386

(22) PCT Filed: May 29, 2013

(86) PCT No.: PCT/EP2013/061017
§ 371 (c)(1),
(2) Date: Dec. 3, 2014

(87) PCT Pub. No.: WO2013/182457
PCT Pub. Date: Dec. 12, 2013

(65) Prior Publication Data
US 2015/0144134 A1    May 28, 2015

(30) Foreign Application Priority Data

Jun. 4, 2012  (CH) ........................ 0767/12

(51) Int. Cl.
*A61M 16/00* (2006.01)
*A61M 16/04* (2006.01)
*A61M 16/08* (2006.01)
*B29C 45/36* (2006.01)

(52) U.S. Cl.
CPC ........ *A61M 16/0447* (2014.02); *A61M 16/04* (2013.01); *A61M 16/0409* (2014.02); *A61M 16/0415* (2014.02); *A61M 16/0486* (2014.02); *A61M 16/0816* (2013.01); *B29C 45/36* (2013.01); *A61M 2207/10* (2013.01)

(58) Field of Classification Search
CPC .......... A61M 16/0047; A61M 16/0447; A61M 16/0486; A61M 16/0409; A61M 16/0415; A61M 16/04; A61M 2207/10; B29C 45/36

See application file for complete search history.

(56) References Cited

U.S. PATENT DOCUMENTS

| | | | | |
|---|---|---|---|---|
| 5,391,248 A * | 2/1995 | Brain | ............... | A61M 16/04 128/207.14 |
| 5,711,293 A * | 1/1998 | Brain | ............... | A61M 16/04 128/200.24 |
| 8,220,461 B1 * | 7/2012 | Guerra | ............ | A61M 16/0463 128/200.26 |
| 2001/0015207 A1 * | 8/2001 | Pagan | ............... | A61M 16/04 128/207.15 |

(Continued)

*Primary Examiner* — Steven Douglas
(74) *Attorney, Agent, or Firm* — DWC Law Firm, P.S.; David Chen; Ann W. Speckman

(57) ABSTRACT

Thus far, it has not been possible to produce laryngeal masks having a supraglottic tube as a one-piece unit. If the supraglottic tube (2) is provided with three lumens (4, 5, 6), the center one (6) of which has no passage to the respiration space (10), a solution is proposed. What is proposed is that the center guide lumen is provided with a longitudinal slit (8) extending from the distal end (9) to the laryngeal mask head (3). A connecting web can be attached between two cores or sliders forming the lumens, generating the desired stability in order to maintain the pressing power tool state without deformation.

17 Claims, 3 Drawing Sheets

(56) References Cited

U.S. PATENT DOCUMENTS

| | | | |
|---|---|---|---|
| 2004/0129272 A1* | 7/2004 | Ganesh | A61M 16/04 128/207.14 |
| 2011/0220117 A1* | 9/2011 | Dubach | A61M 16/04 128/207.14 |
| 2012/0090609 A1* | 4/2012 | Dubach | A61M 16/04 128/204.18 |
| 2015/0114400 A1* | 4/2015 | Dubach | A61M 16/04 128/207.15 |

* cited by examiner

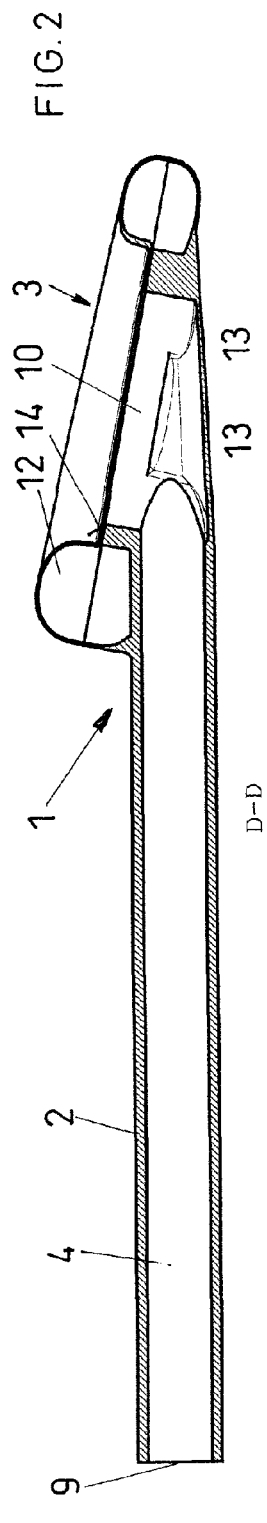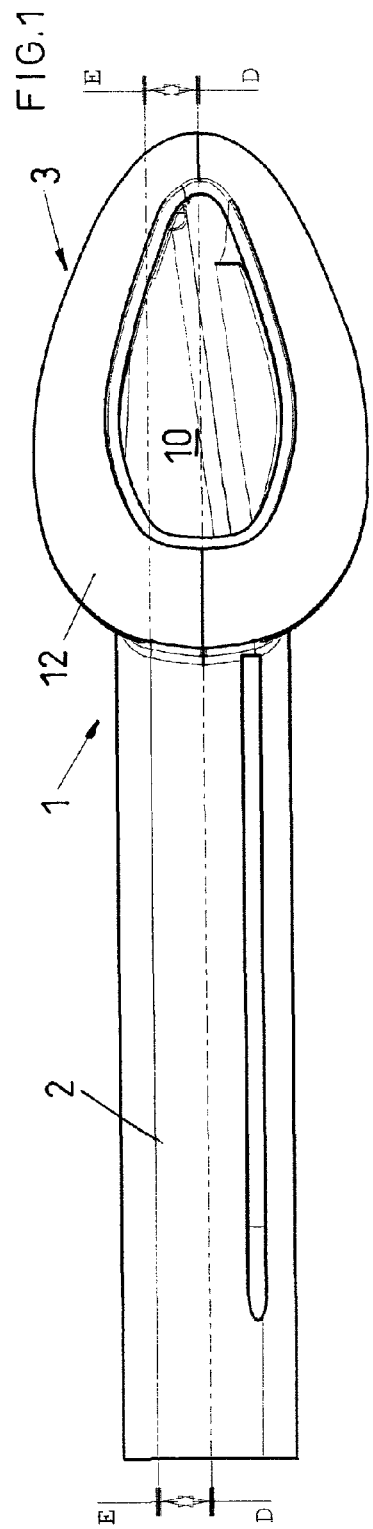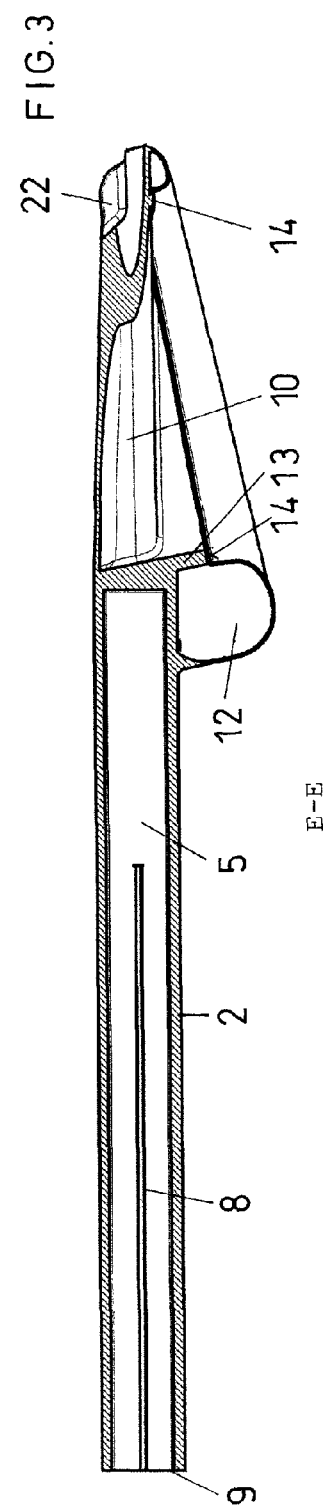

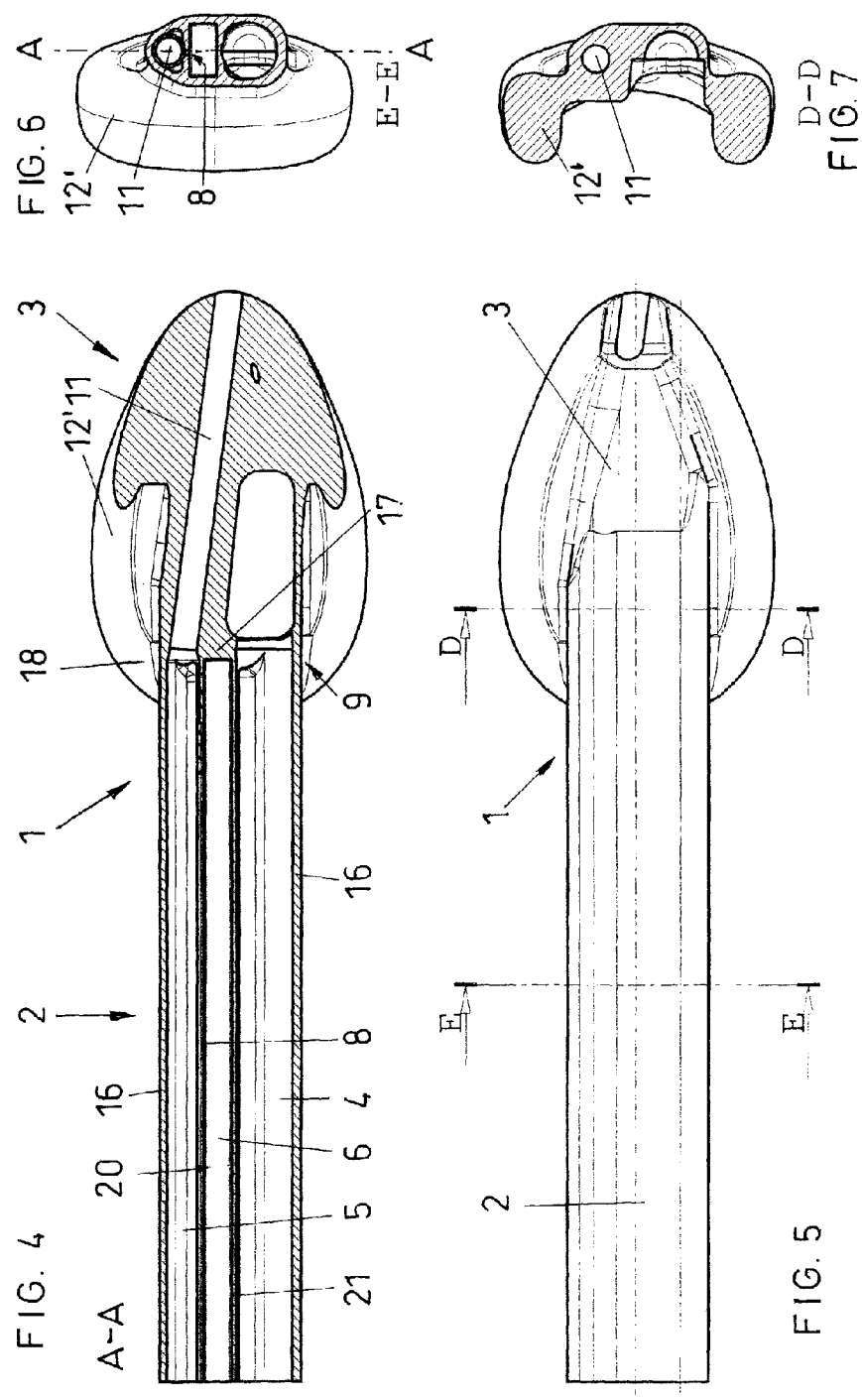

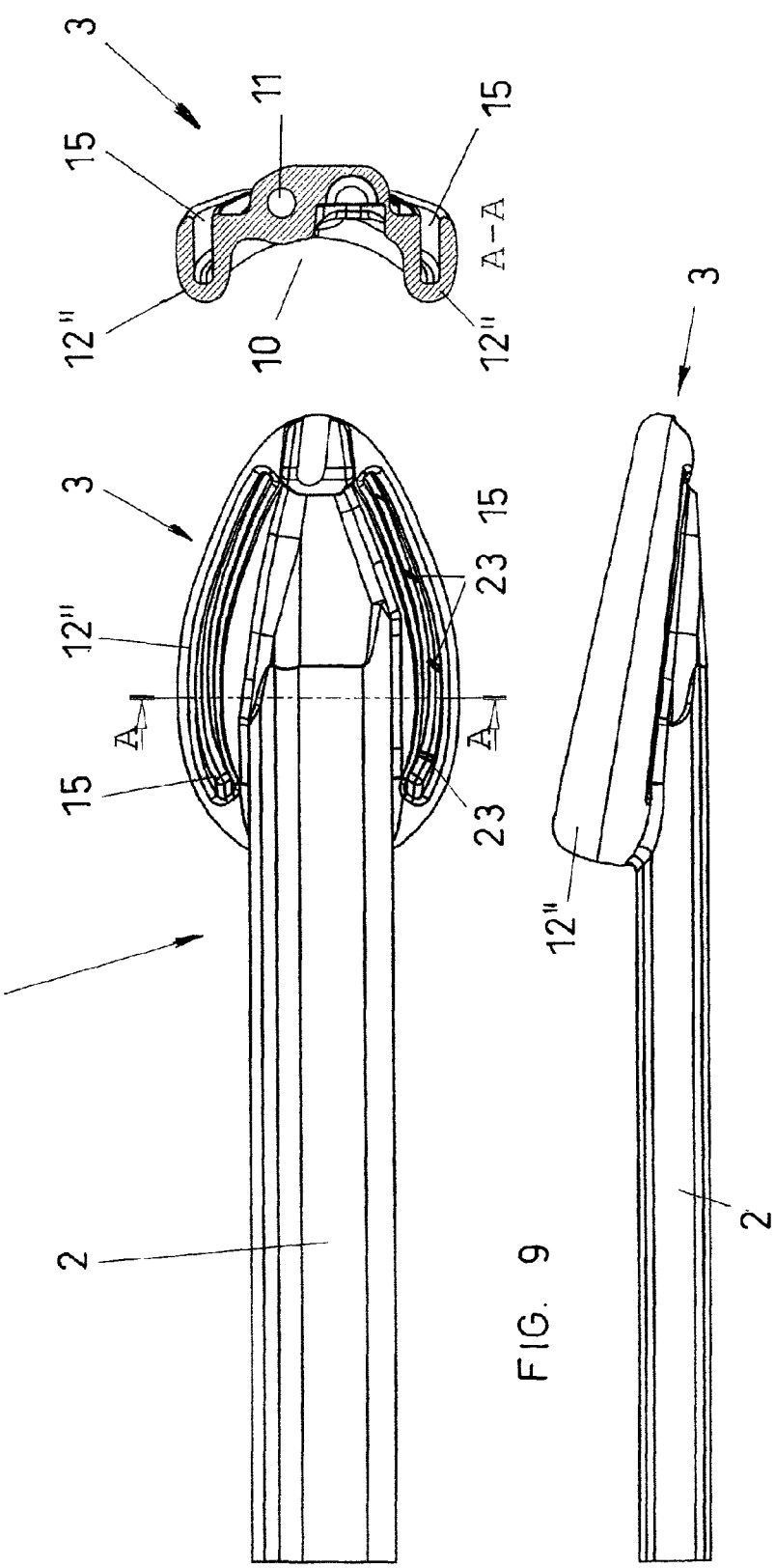

LARYNGEAL MASK HAVING A SUPRAGLOTTIC TUBE

REFERENCE TO RELATED APPLICATIONS

This application is the US national phase entry of International Patent Application no. PCT/EP2013/061017, filed May 29, 2013, which claims priority to Swiss patent application no. 00767/12, filed Jun. 4, 2012.

TECHNICAL FIELD

The present invention relates to a laryngeal mask having a supraglottic tube for insertion of a laryngeal mask head over the larynx, where the supraglottic tube has three lumens, namely a respiration lumen, which serves to supply respiration air and the instrumentation, an esophageal lumen, which serves to provide esophageal access and a guide lumen, which runs medially in between the two former lumens and is closed at the proximal end.

BACKGROUND

Laryngeal masks are made of plastic and are usually used only once. A laryngeal mask usually consists of a supraglottic tube and a laryngeal mask head. These two parts are manufactured separately and then joined together by welding or by gluing. A typical example of such a laryngeal mask is shown in US 2003/037790. The supraglottic tube here has two parallel lumens, where the one lumen is the respiration lumen and the wide lumen is the esophageal lumen. On the other hand, US 2006/032505 describes a supraglottic tube, which is formed by three tubes running side by side. US 2007/028923 discloses a laryngeal mask, in which the supraglottic tube has a central respiration lumen and is shown in the wall dorsally and ventrally, each tube with a small diameter. Although neither the description nor the drawings indicate that the tube and the laryngeal mask head were manufactured separately, the construction alone leaves no other conclusion. The current shape of the tube makes it impossible to extract a core forming the lumen. Likewise, the tube, which has the lumen embedded in the wall, cannot be manufactured by any other method than extrusion or extrusion molding. Such a thick-walled tubing can also be shaped later by a heat treatment, if desired.

The invention is directed to a laryngeal mask according to WO 2010/060227. This laryngeal mask has a supraglottic tube, to which the laryngeal mask head is attached. Accordingly, the laryngeal mask head has a receiving bushing, into which the tube is inserted and can be welded or glued to the laryngeal mask head. Such a manufacturing process requires a great deal of manual work and thus is time-consuming and cost intensive accordingly. The supraglottic tube used here is manufactured by injection molding. Likewise, the laryngeal mask head is manufactured with a second injection molding form, also in two parts. The supraglottic tube, which usually has a length of approx. 20 cm, can therefore be manufactured by injection molding because, on the one hand, the wall thicknesses do not have any relevant differences in thickness and because, on the other hand, the cores forming the lumen are held movably as pulls or slides in a part of the mold while the ends of the cores can be held in an absolutely and force-fitting and form-fitting manner in another part of the mold and thus there cannot be any deformation of the cores. It therefore seems self-evident to manufacture the supraglottic tube as well as the laryngeal mask head together in one piece. However, this has seemingly not been found to be feasible in the past because corresponding movable cores are required in both the supraglottic tube and the laryngeal mask head, and these cores cannot be secured in a form-fitting and force-locking manner in the opposing part of the mold. At the prevailing pressure in such plastic injection molds, the cores cannot easily be pressed flatly at their ends. If with such a design, the mold to be filled with plastic, the cores would no longer close satisfactorily at the prevailing pressures or the pressures that occur, at the latest after a few thousand opening and closing operations of the injection mold and films or membranes, as they are known in the technical jargon would form on the abutting parts of the cores. In other words, the finished laryngeal masks would have to be tested to determine that both the respiration lumen and the esophageal lumen have unhindered passage. However, this would again require additional steps, additional test equipment and would thus cause increased costs. Therefore the object of the present invention is to manufacture a laryngeal mask made of plastic in one piece while avoiding the problems described above.

SUMMARY

This object is achieved by a laryngeal mask of the type defined in the introduction, which is characterized in that the supraglottic tube and the laryngeal mask are manufactured in one piece by injection molding, with a slot connecting the two lumens running over at least a portion of the length of the supraglottic tube from the proximal end.

As mentioned above, this slot according to the invention can be formed only when the injection mold, which is required for this purpose, has a web between each core to form the guide lumen and one of the neighboring cores, wherein these two cores are interconnected by means of a stabilizing web from the proximal end in the distal direction.

Thanks to this approach, the core in particular is additionally stabilized to form the guide lumen, which is especially important because this core is a so-called flying core, which is not supported on the opposite mold part or on an opposing core. Only in this way can the guide lumen, which is closed distally, be formed.

Since the laryngeal masks known in the past have not had any medial guide lumen, except for the approach according to WO 2010/060227, with the laryngeal masks that are otherwise known, such an approach cannot be implemented. For example if the supraglottic tube consists only of a respiration lumen and an esophageal lumen running parallel thereto, then there need not be any further connection between these two lumens, i.e., in particular no slot need be present connecting these two lumens, so that the material to be sucked out through the esophageal lumen must not enter the respiration lumen. Only in the case of a laryngeal mask having a supraglottic tube, as described in the introduction, can the problem according to the invention be solved.

The drawing illustrates various embodiments in which the differentiation consists essentially only of the design of the laryngeal head. It should be pointed out clearly here that the approach according to the invention is suitable for a variety of types of laryngeal masks, as long as they have a supraglottic tube of the type defined in the introduction.

BRIEF DESCRIPTION OF THE DRAWINGS

The drawings show preferred exemplary embodiments of the subject matter of the present invention and these embodiments are explained on the basis of the following description with reference to the drawings, in which:

FIG. 1 shows a one-piece laryngeal mask with a view to the ventral side.

FIG. 2 shows a central vertical section along the line D-D in FIG. 1, and FIG. 3 shows a similar section along the line E-E with a view to the dividing wall between the esophageal lumen and the guide lumen, wherein FIGS. 1 through 3 show diagrams of a laryngeal mask with an inflatable cuff.

FIG. 4 shows a laryngeal mask in a horizontal section, wherein this is a laryngeal mask, in which the cuff is manufactured without a cavity, i.e., it is made of a solid material.

FIG. 5 shows the same laryngeal mask according to FIG. 4 in a view of the laryngeal mask from the dorsal side.

FIG. 6 shows the laryngeal mask in a section along line E-E in FIG. 5, wherein the supraglottic tube is cut at a right angle to its longitudinal direction, while the laryngeal mask head is shown in a view outward from this sectional surface.

FIG. 7 shows the laryngeal mask head in a vertical section along line D-D in FIG. 5.

FIGS. 8 through 10 show a variant of the laryngeal mask according to FIGS. 4 through 7, but the laryngeal mask head here is designed to be resilient in the medial-lateral direction.

FIG. 8 shows this laryngeal mask in a dorsal view and

FIG. 9 shows the mask in a lateral view, while

FIG. 10 shows a vertical section through the laryngeal mask head along line A-A in FIG. 8.

DETAILED DESCRIPTION

The terms used below for determining the position relate to the position of the laryngeal mask in relation to the patient. Accordingly, "distal(ly)" means located at a distance from the center of the patient's body, while "proximal(ly)" is directed toward the center of the patient's body. Accordingly, "lateral(ly)" here means facing away from the center of the body, while "medial(ly)" means toward the center of the body.

In this patent application, the term "laryngeal mask" is understood to apply to the totality consisting of the supraglottic tube and the laryngeal mask head connected to the former. Consequently, the laryngeal mask, i.e., the entirety thereof, consists of the supraglottic tube 2 and the laryngeal mask head 3 connected to the former in one piece.

The supraglottic tube is therefore the tube that can be guided over, i.e., above the glottis. The supraglottic tube 2 has a plurality of lumens. In the embodiment according to the invention, the supraglottic tube 2 has three lumens. Reference is made to FIG. 4 in this regard. The lumen having the largest diameter, i.e., with the largest inside clearance is the respiration lumen 4 positioned laterally. It borders on the guide lumen 6 that runs medially. The lateral esophageal lumen 5 in turn thus runs laterally on the other side of the guide lumen 6. The cross section of the supraglottic tube 2 can be seen in the sectional view in FIG. 6, where this section runs along line E-E in FIG. 5. This FIG. 5 shows the laryngeal mask 1 with a view toward the ventral side of the laryngeal mask. FIG. 4 shows a horizontal section running at the center of the height of the supraglottic tube 2. This sectional plane A-A is shown in FIG. 6.

The supraglottic tube 2 develops into the laryngeal mask head 3 without a separating line. The region in which the supraglottic tube 2 develops into the laryngeal mask head 3 is referred to as the transitional area 18. The proximal end wall 17, which seals the guide lumen 6 proximally, is present in this transitional area 18. In the same transitional area 18, the esophageal lumen 5 develops into the esophageal passage 11 in the region of the laryngeal mask head 3. This esophageal passage 11 runs above the respiration space 10, which can be seen most clearly in FIG. 7, which shows a section through the laryngeal mask head 3 in the region of the sectional line D-D in FIG. 5. This figure also shows the esophageal passage 11 as a cylindrical hole running above the respiration space 10, as mentioned above. FIG. 4 also shows clearly that the esophageal passage 11 extends through the laryngeal mask head 3 absolutely in a straight line, and this esophageal passage 11 ends in the esophageal lumen 5 in the above-mentioned transitional area 18. This yields a location of a change in direction 19 in the transitional area 18. This diagram also shows clearly that the length of the esophageal passage 11 corresponds approximately to one-third or more of the length of the supraglottic tube 2.

In the same transitional area 18, the respiration lumen 4 also opens into the respiration space 10, as can be seen in FIG. 4 as well as in FIG. 7. This embodiment according to FIGS. 4 through 6 relates to an approach in which the cuff 12 is designed as a cuff 12' without any cavities. A cuff 12' without any cavities yields a somewhat increased strength, which facilitates insertion of the laryngeal mask into the patient. Laryngeal masks of this design are appropriate for use in the emergency field in particular.

FIGS. 1 through 3 illustrate a laryngeal mask in an inflatable cuff 12'. The approach illustrated here, which is used in the clinical field today in particular, is also manufactured in one piece. Here again, the laryngeal mask is labeled as 1 on the whole, whereas the supraglottic tube is labeled as 2 and the laryngeal mask head is labeled as 3. The laryngeal mask 1 is shown here in the condition in which the laryngeal mask 1 comes out of the injection mold. The cuff 12 is still open accordingly and must be closed by welding or adhesive bonding. The cuff 12 surrounds the respiration space 10 and ends in an inwardly directed welded edge 14, i.e., pointing toward the center of the respiration space 10. The respiration space 10 per se is bordered by a peripheral adhesive wall and/or welded wall 13. The above-mentioned collar-type adhesive edge and/or welded edge 14 is glued or welded onto the adhesive wall and/or welded wall 13 to form a seal in the completely installed state. The slot 8 according to the invention can be seen more clearly in FIG. 3 in particular than in the versions according to FIGS. 4 through 7. This slot 8 runs from the distal end 9 of the supraglottic tube 2 toward the laryngeal mask head 3 in the proximal direction. The length of this slot 8 amounts to at least one-third of the total length of the supraglottic tube 2. The slot 8 may be arranged in one of the two dividing walls 20, 21 either in dividing wall 20, which separates the guide lumen 6 from the esophageal lumen 5, or in the dividing wall 21, which separates the guide lumen 6 from the respiration lumen 4. In the embodiment according to FIGS. 1 to 3 as well as in the version according to FIGS. 4 through 7, the slot runs in the dividing wall 20, separating the guide lumen 6 from the esophageal lumen 5. In both versions the esophageal lumen passage opens upstream from the cuff 12 on the proximal end of the laryngeal mask and runs over the cuff in an open channel 22. The slot 8 is formed spontaneously due to the fact that a connecting web is present in the injection mold between its core, which forms one of the two lateral lumens 4 or 5, and the medial guide lumen 6. Owing to this web, the two cores having the smallest diameters are supported with respect to one another and are reinforced accordingly. However, since the medial core of the injection mold in particular is problematical because it cannot be supported on an opposing core, the slot 8 can also run in the dividing wall 21 between the guide lumen 6 and the respiration lumen 4. The core of the injection mold, with which the laryngeal mask according to the invention is manufactured, is designed so that an additional core, with which the esophageal passage 11 is formed, can engage with the core forming the esophageal lumen 5 in a form-fitting manner in the impact region. Accordingly, the one core has a hole on its end, which faces the other core, and the other core has a pin, which fits in it in a form-fitting manner, so that these two cores secure one another mutually with a reinforcing effect.

In a last embodiment of the invention, which also relates to a laryngeal mask manufactured in one piece, and the supraglottic tube 2 is designed exactly the same as those in the two embodiments described above, a laryngeal mask head 3 with a cuff 12" of a different design is shown. This approach combines the advantages of the two approaches described above with the cuff 12 and/or with the approach according to the cuff 12'. This is not an inflatable cuff but instead is a cuff, which basically has no cavities but nevertheless is shaped to be resilient in the medial-lateral direction. Here again, the same parts are labeled with the same reference numerals as in the variant described previously. The cuff 12" here has a spring channel 15 having a U-shaped cross section in its peripheral contour line in the lateral region. This spring channel allows the outer lateral wall regions to be elastic from laterally to medially. This allows an adjustment in the width of the laryngeal mask head without it having to be inflated. The spring force of the adjustment in the lateral-medial direction can be adjusted with additional design means. To this end, a plurality of thin spring walls 23 running across the direction of the spring channel 15 may also be molded in the spring channel 15, which has a U-shaped cross section (see FIG. 8). Such spring walls 23 may be arranged at a right angle to the longitudinal direction of the spring channel 18 or may also run obliquely to the longitudinal direction thereof, as shown here in the drawing. Likewise such spring walls need not run in a straight line but may also have a curved shape, an arc shape or an S-shape. All these variants yield possibilities for adjusting the spring force.

The various embodiments should merely prove that the concept of the one-piece production of the laryngeal mask allows many variants with respect to the design of the laryngeal mask head. However, permitting a knowledge base about such a one-piece production at all is based on the fact that one of the two dividing walls between one of the two lateral lumens, namely the respiration lumen 4 or the esophageal lumen 5, and the medial guide lumen 6 is connected to the other by means of a slot 8.

LIST OF REFERENCE NUMERALS

1 laryngeal mask
2 tube
3 laryngeal mask head
4 respiration lumen
5 esophageal lumen
6 guide lumen
7 proximal end
8 slot
9 distal end
10 respiration space
11 esophageal passage
12 cuff
12' cuff
12" cuff
13 welded wall
14 welded edge
15 spring channel
16 lateral wall
17
18 transitional area
19 location the change in direction

The invention claimed is:

1. A laryngeal mask comprising a supraglottic tube configured for insertion of a laryngeal mask head over a larynx, wherein the supraglottic tube comprises:
   (a) a respiration lumen which serves to supply respiration air and for instrumentation, (b) an esophageal lumen, which serves to provide esophageal access, and (c) a guide lumen that runs medially in between the respiration lumen and the esophageal lumen and is closed at a proximal end,
   wherein
   the supraglottic tube and the laryngeal mask head are manufactured by injection molding in one piece, and wherein a connecting slot, which connects the guide lumen and at least one of the respiration lumen and the esophageal lumen, runs over at least a portion of the length of the supraglottic tube from a distal end and runs between the at least one of the respiration lumen and the esophageal lumen and the guide lumen.

2. The laryngeal mask according to claim 1, wherein the connecting slot connects the respiration lumen with the guide lumen.

3. The laryngeal mask according to claim 1, wherein the connecting slot connects the esophageal lumen to the guide lumen.

4. The laryngeal mask according to claim 1, wherein the length of the connecting slot extends at least over one-fourth of the total length of the supraglottic tube from the proximal end to the distal end.

5. The laryngeal mask according to claim 1, wherein the laryngeal mask has a central respiration space in the laryngeal mask head, in which the respiration lumen of the supraglottic tube ends, and above the respiration space there is an esophageal passage in which the esophageal lumen opens, and the respiration space is surrounded by a cuff.

6. The laryngeal mask according to claim 5, wherein the cuff is an inflatable cuff.

7. The laryngeal mask according to claim 5, wherein the respiration space is bordered by a peripheral adhesive wall, and the cuff has a peripheral collar type adhesive edge, which is adapted to a shape and a size of the adhesive wall bordering the respiration space and, in a completely assembled state, is connected to the adhesive wall bordering the respiration space with a seal.

8. The laryngeal mask according to claim 5, wherein the cuff consists of solid material without any cavities.

9. The laryngeal mask according to claim 8, wherein at least one spring channel, which increases compressibility in a medial-lateral direction, is molded on a dorsal side of the cuff running at least in a longitudinal direction along at least one lateral edge of the cuff.

10. The laryngeal mask according to claim 9, wherein
the at least one spring channel is molded along each of two lateral walls of the cuff, at least approximately parallel to same.

11. The laryngeal mask according to claim 1, wherein
the guide lumen is closed with respect to the laryngeal mask head in a transitional area on a distal end of the supraglottic tube, the respiration lumen develops into a respiration space in the transitional area, and a location of a change in direction exists in the transitional area at a location where the esophageal lumen develops into an esophageal passage.

12. An injection mold for production of a laryngeal mask having a supraglottic tube according to claim 1, wherein
to form the supraglottic tube there are three parallel cores, wherein a first core to form the guide lumen and a second neighboring core are connected to one another by a stabilizing web from the proximal end in a distal direction.

13. The injection mold according to claim 12, wherein
two cores forming the respiration space and the esophageal passage running above it are parts of a first injection mold half, and three cores forming the lumens of the supraglottic tube are part of a second injection mold half.

14. The injection mold according to claim 12, wherein
the core forming the esophageal lumen and the core forming the esophageal passage engage in one another in a form-fitting manner in the direction of a closing movement in a closing region of the two injection mold halves.

15. The injection mold according to claim 13, wherein
the core forming the respiration space and the core forming the respiration lumen engage in one another in a form-fitting manner in the direction of a closing movement in a closing region of the two injection mold halves.

16. The injection mold according to claim 12, wherein
the cores forming the lumens are slidable.

17. The laryngeal mask according to claim 5, wherein
the respiration space is bordered by a welded wall, and the cuff has a peripheral collar type welded edge, which is adapted to a shape and a size of the welded wall bordering the respiration space and, in a completely assembled state, is connected to the welded wall bordering the respiration space with a seal.

* * * * *